US007669595B1

(12) United States Patent
Mitchell

(10) Patent No.: US 7,669,595 B1

(45) Date of Patent: Mar. 2, 2010

(54) JUNCTION DEVICE

(76) Inventor: Bryon L. Mitchell, 1228 N. Legion Dr., Tahlequah, OK (US) 74464

( * ) Notice: Subject to any disclaimer, the term of this patent is extended or adjusted under 35 U.S.C. 154(b) by 961 days.

(21) Appl. No.: 11/396,118

(22) Filed: Apr. 3, 2006

(51) Int. Cl.
*A61M 11/00* (2006.01)

(52) U.S. Cl. ............................ 128/203.12; 128/200.14; 128/200.21

(58) Field of Classification Search ............ 128/200.14, 128/200.21, 203.12, 203.15, 203.16, 204.18, 128/205.24; 285/179, 272, 275, 278, 98
See application file for complete search history.

(56) References Cited

U.S. PATENT DOCUMENTS

| | | | | |
|---|---|---|---|---|
| 1,941,174 | A * | 12/1933 | Jensen | 137/801 |
| D285,496 | S | 9/1986 | Berman | |
| 5,474,059 | A | 12/1995 | Cooper | |
| 5,586,551 | A | 12/1996 | Hilliard | |
| 5,694,922 | A | 12/1997 | Palmer | |
| 5,701,886 | A | 12/1997 | Ryatt | |
| 5,765,553 | A | 6/1998 | Richards et al. | |
| 6,012,455 | A | 1/2000 | Goldstein | |
| 6,340,023 | B2 * | 1/2002 | Elkins | 128/200.21 |
| 7,191,776 | B2 * | 3/2007 | Niles et al. | 128/200.14 |
| 7,448,376 | B2 * | 11/2008 | Lepel | 128/200.14 |
| 2006/0231091 | A1 * | 10/2006 | Camarillo | 128/200.21 |

* cited by examiner

*Primary Examiner*—Steven O Douglas

(57) ABSTRACT

A junction device for administering nebulizer treatments directly to a supply of oxygen supplied to a patient mask includes a supply conduit being couplable to an oxygen supply and a patient mask to allow oxygen from the oxygen supply to be supplied to the patient mask. A side conduit is coupled to and is in fluid communication with the supply conduit. An elbow conduit is rotatably coupled to the side conduit opposite the supply conduit. The elbow conduit is couplable to a nebulizer to permit treatments from the nebulizer to flow through the elbow conduit and the side conduit into the oxygen being supplied to the patient mask. A valve assembly is positioned in the elbow conduit between the side conduit and the nebulizer. The valve assembly opens and closes to control the treatments from the nebulizer to flowing into the elbow conduit.

17 Claims, 3 Drawing Sheets

JUNCTION DEVICE

BACKGROUND OF THE INVENTION

1. Field of the Invention

The present invention relates to patient mask supply junctions and more particularly pertains to a new patient mask supply junction for administering nebulizer treatments directly to a supply of oxygen supplied to a patient mask.

2. Description of the Prior Art

The use of patient mask supply junctions is known in the prior art. The prior art commonly teaches a patient mask having several connections to allow multiple treatment machines to be coupled to the patient mask and thus uses the patient mask to mix treatments provided from the treatment machines.

While these devices fulfill their respective, particular objectives and requirements, the need remains for a device that has certain improved features that allow treatments from a nebulizer to be provided directly to a supply of oxygen supplied to a patient mask prior to the oxygen supply reaching the patient mask. Additionally, the nebulizer may be positioned at a variety of angles to enhance the comfort of a patient wearing the patient mask.

SUMMARY OF THE INVENTION

The present invention meets the needs presented above by generally comprising a supply conduit being couplable to an oxygen supply and a patient mask to allow oxygen from the oxygen supply to be supplied to the patient mask. A side conduit is coupled to and is in fluid communication with the supply conduit. The side conduit extends substantially orthogonal to the supply conduit. An elbow conduit is rotatably coupled to the side conduit opposite the supply conduit. The elbow conduit is couplable to a nebulizer to permit treatments from the nebulizer to flow through the elbow conduit and the side conduit into the oxygen being supplied to the patient mask. A valve assembly is positioned in the elbow conduit between the side conduit and the nebulizer. The valve assembly opens to permit the treatments from the nebulizer to flow into the elbow conduit when air pressure from the nebulizer is greater than an air pressure in the supply conduit. The valve assembly closes to inhibit the treatments from entering the elbow conduit when the air pressure in the supply conduit is greater than the air pressure from the nebulizer.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
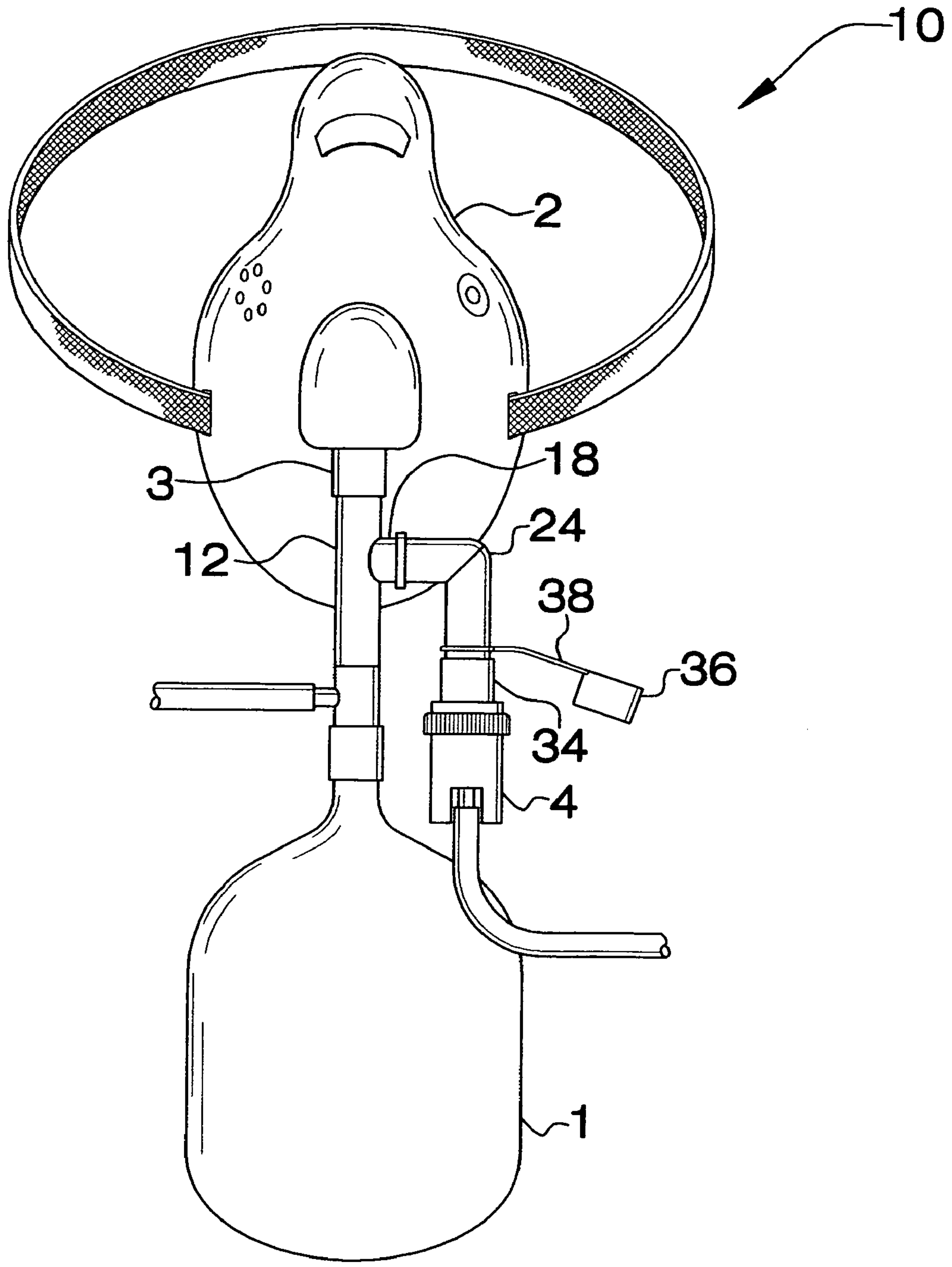
FIG. 1 is a front view of a junction device according to the present invention shown in use with an oxygen supply, a patient mask and nebulizer.
Figure 2:
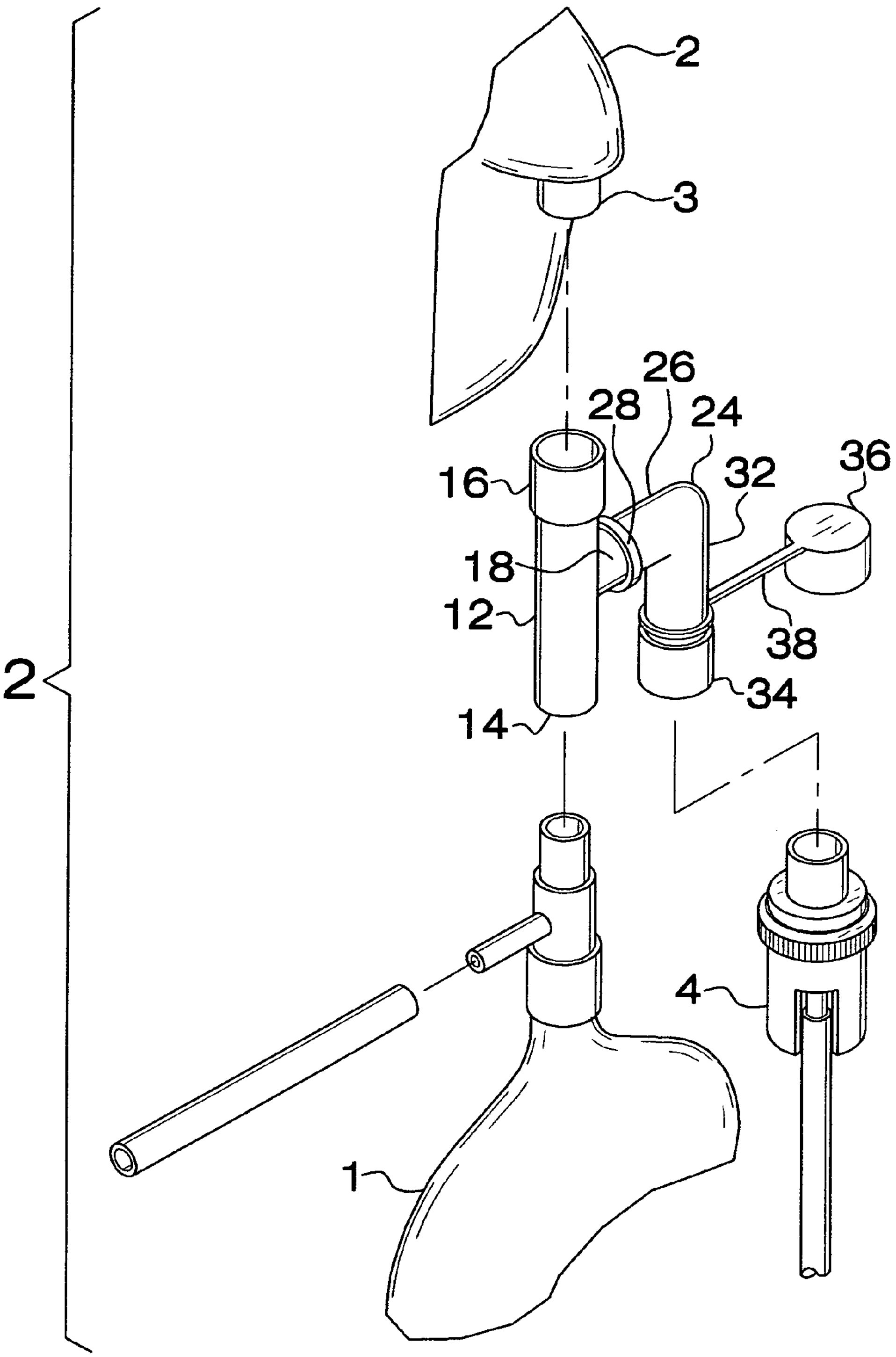
FIG. 2 is an exploded perspective view of the present invention.
Figure 3:
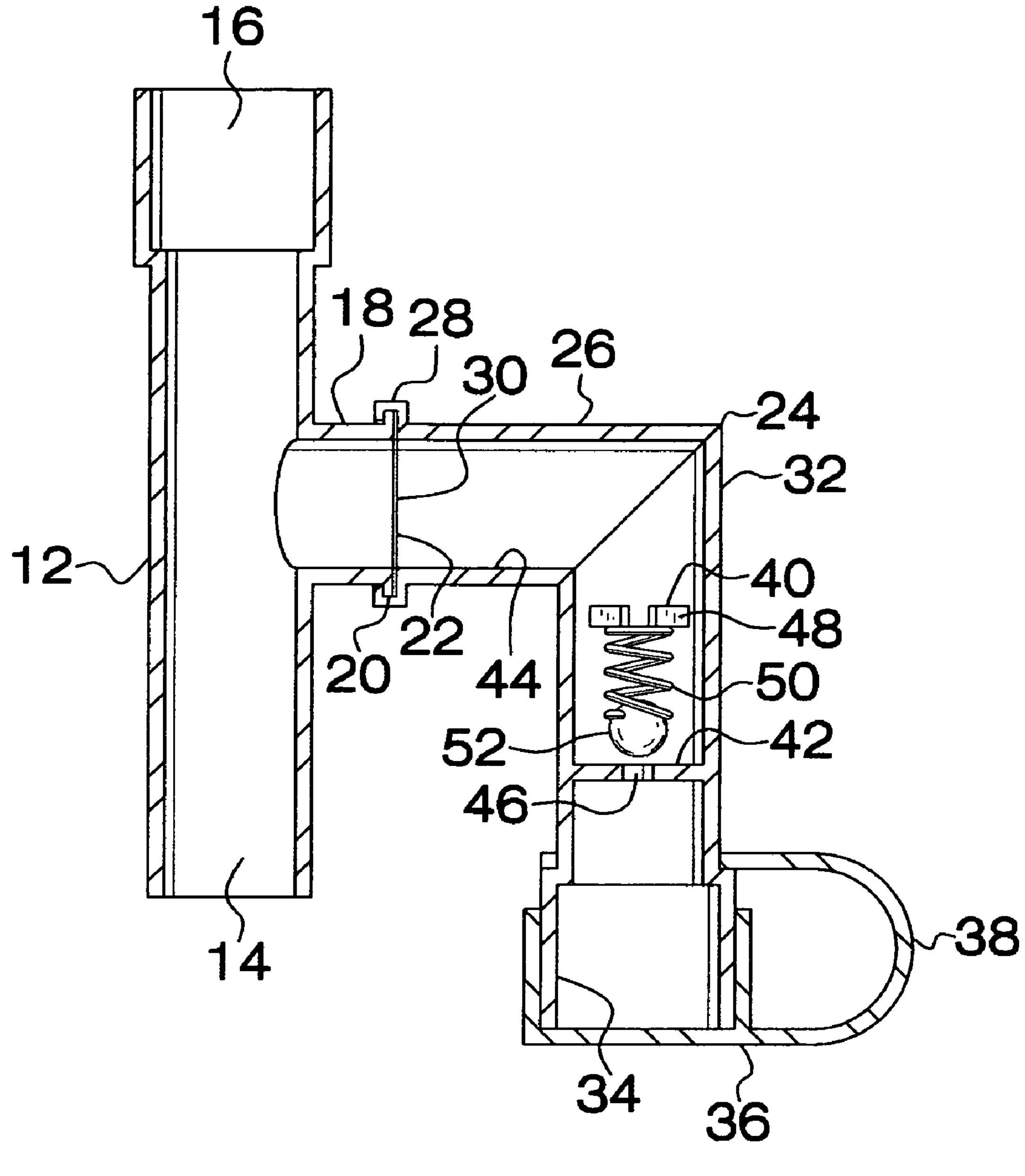
FIG. 3 is a cross-sectional view of the present invention.

With reference now to the drawings, and in particular to FIGS. 1 through 3 thereof, a new patient mask supply junction embodying the principles and concepts of the present invention and generally designated by the reference numeral 10 will be described.

As best illustrated in FIGS. 1 through 3, the junction device 10 generally comprises a supply conduit 12 being couplable to an oxygen supply 1 and a patient mask 2 to allow oxygen from the oxygen supply 1 to be supplied to the patient mask 2. The supply conduit 12 includes a first end 14 being received by the oxygen supply 1. The supply conduit 12 includes a second end 16 positioned opposite the first end 14. The second end 16 receives an inlet port 3 of the patient mask 2 to allow oxygen supplied to the supply conduit 12 to be supplied to a patient wearing the patient mask 2.

A side conduit 18 is coupled to and is in fluid communication with the supply conduit 12. The side conduit 18 extends substantially orthogonal to the supply conduit 12. The side conduit 18 is positioned between the first end 14 and the second end 16 of the supply conduit 12. The side conduit 18 includes a flange 20 being coextensive and extending outwardly from a free end 22 of the side conduit 18.

An elbow conduit 24 is rotatably coupled to the side conduit 18 opposite the supply conduit 12. The elbow conduit 24 is couplable to a nebulizer 4 to permit treatments from the nebulizer 4 to flow through the elbow conduit 24 and the side conduit 18 into the oxygen being supplied to the patient mask 2. The elbow conduit 24 includes a first portion 26 rotatably coupled to the free end 22 of the side conduit 18 to permit rotational adjustment of the elbow conduit 24 with respect to the side conduit 18. The first portion 26 is axially aligned with the side conduit 18. The first portion 26 includes a flange collar 28 for receiving and extending around the flange 20 of the side conduit 18 to rotatably couple the elbow conduit 24 to the side conduit 18.

The elbow conduit 24 also includes a seal 30 positioned between the flange 20 of the side conduit 18 and the flange collar 28 of the elbow conduit 24. The seal 30 inhibits fluid communication between an environment and the treatments passing through the elbow conduit 24 and the side conduit 18. A second portion 32 is coupled to the first portion 26 opposite the side conduit 18. The second portion 32 extends substantially orthogonal to the first portion 26. A receiving collar 34 is coupled to the second portion 32 opposite the first portion 26. The receiving collar 34 receives the nebulizer 4 to selectively mount the nebulizer 4 to the elbow conduit 24 and permit treatments to be supplied to the elbow conduit 24.

The elbow conduit 24 additionally includes a cap 36 couplable to the receiving collar 34 to selectively close the receiving collar 34 when the nebulizer 4 is removed from the receiving collar 34. A tether 38 is coupled to the cap 36 and extends around the second portion 32. The tether 38 inhibits loss of the cap 36 when the cap 36 is removed from the receiving collar 34.

A valve assembly 40 is positioned in the elbow conduit 24 between the side conduit 18 and the nebulizer 4. The valve assembly 40 opens to permit the treatments from the nebulizer 4 to flow into the elbow conduit 24 when air pressure from the nebulizer 4 is greater than an air pressure in the supply conduit 12. The valve assembly 40 closes to inhibit the treatments from entering the elbow conduit 24 when the air pressure in the supply conduit 12 is greater than the air pressure from the nebulizer 4.

The valve assembly 40 includes a partition wall 42 coupled to the second portion 32 and extending across a bore 44 of the elbow conduit 24. The partition wall 42 has a treatment aperture 46 permitting the treatments from the nebulizer 4 to pass through the partition wall 42. The partition wall 42 is positioned adjacent the receiving collar 34. A base wall 48 is coupled to the second portion 32 and is positioned in the bore 44 of the elbow conduit 24. The base wall 48 is positioned adjacent the first portion 26.

The valve assembly 40 also includes a biasing member 50 coupled to the base wall 48 and extends towards the partition wall 42. A closure member 52 is coupled to the biasing member 50 opposite the base wall 48. The closure member 52 is biased into the treatment aperture 46 of the partition wall 42 to close the treatment aperture 46 when the air pressure in the supply conduit 12 is greater than the air pressure from the nebulizer 4. The closure member 52 is forced out of the treatment aperture 46 to open the treatment aperture 46 to allow treatments to pass through the partition wall 42 when the air pressure from the nebulizer 4 is greater than the air pressure in the supply conduit 12.

In use, the oxygen supply 1 is coupled to the first end 14 of the supply conduit 12 and the patient mask 2 to the second end 16. The nebulizer 4 is coupled to the receiving collar 34 of the elbow conduit 24 to receive treatments from the nebulizer 4. The valve assembly 40 opens to allow the treatments from the nebulizer 4 to flow into the elbow conduit 24 and into the supply conduit 12 when the air pressure in the supply conduit 12 is reduced by the patient inhaling. The valve closes to inhibit introduction of the treatments into the elbow conduit 24 when the patient exhales and the air pressure in the supply conduit 12 is greater than the air pressure from the nebulizer 4.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A junction device for connecting an oxygen supply and a nebulizer to a patient mask, said device comprising:

a supply conduit being couplable to the oxygen supply and the patient mask to allow oxygen from the oxygen supply to be supplied to the patient mask;

a side conduit being coupled to and being in fluid communication with said supply conduit, said side conduit extending substantially orthogonal to said supply conduit;

an elbow conduit being rotatably coupled to said side conduit opposite said supply conduit, said elbow conduit being couplable to the nebulizer to permit treatments from the nebulizer to flow through said elbow conduit and said side conduit into the oxygen being supplied to the patient mask; and a valve assembly being positioned in said elbow conduit between said side conduit and the nebulizer, said valve assembly opening to permit the treatments from the nebulizer to flow into said elbow conduit when air pressure from the nebulizer is greater than an air pressure in said supply conduit, said valve assembly closing to inhibit the treatments from entering said elbow conduit when the air pressure in said supply conduit is greater than the air pressure from the nebulizer.

2. The device according to claim 1, wherein said supply conduit includes a first end being received by the oxygen supply, said supply conduit including a second end positioned opposite said first end, said second end receiving an inlet port of the patient mask to allow oxygen supplied to said supply conduit to be supplied to a patient wearing the patient mask.

3. The device according to claim 2, wherein said side conduit is positioned between said first end and said second end of said supply conduit.

4. The device according to claim 1, wherein said side conduit includes a flange being coextensive and extending outwardly from a free end of said side conduit.

5. The device according to claim 4, wherein said elbow conduit includes a flange collar for receiving and extending around said flange of said side conduit to rotatably couple said elbow conduit to said side conduit.

6. The device according to claim 5, wherein said elbow conduit includes a seal being positioned between said flange of said side conduit and said flange collar of said elbow conduit, said seal inhibiting fluid communication between an environment and the treatments passing through said elbow conduit and said side conduit.

7. The device according to claim 1, wherein said elbow conduit includes a first portion being rotatably coupled to said side conduit to permit rotational adjustment of said elbow conduit with respect to said side conduit.

8. The device according to claim 7, wherein said first portion is axially aligned with said side conduit.

9. The device according to claim 7, wherein said elbow conduit includes a second portion coupled to said first portion opposite said side conduit, said second portion extending substantially orthogonal to said first portion, said valve assembly being positioned in said second portion.

10. The device according to claim 9, wherein said elbow conduit includes a receiving collar being coupled to said second portion opposite said first portion, said receiving collar receiving the nebulizer to selectively mount the nebulizer to said elbow conduit and permit treatments to be supplied to said elbow conduit.

11. The device according to claim 10, wherein said elbow conduit includes a cap being couplable to said receiving collar to selectively close said receiving collar when the nebulizer is removed from said receiving collar.

12. The device according to claim 11, wherein said elbow conduit includes a tether being coupled to said cap and extending around said second portion, said tether inhibiting loss of said cap when said cap is removed from said receiving collar.

13. The device according to claim 1, wherein said valve assembly includes a partition wall being coupled to said elbow conduit and extending across a bore of said elbow conduit, said partition wall having a treatment aperture permitting the treatments from the nebulizer to pass through said partition wall.

14. The device according to claim 13, wherein said valve assembly includes a base wall coupled to said elbow conduit and being positioned in said bore of said elbow conduit.

15. The device according to claim 14, wherein said valve assembly includes a biasing member coupled to said base wall and extending towards said partition wall.

16. The device according to claim 15, wherein said valve assembly includes a closure member being coupled to said biasing member opposite said base wall, said closure member being biased into said treatment aperture of said partition wall to close said treatment aperture when the air pressure in said supply conduit is greater than the air pressure from the nebulizer, said closure member being forced out of said treatment aperture to open said treatment aperture to allow treatments to pass through said partition wall when the air pressure from the nebulizer is greater than the air pressure in said supply conduit.

17. A junction device for connecting an oxygen supply and a nebulizer to a patient mask, said device comprising:

a supply conduit being couplable to the oxygen supply and the patient mask to allow oxygen from the oxygen supply to be supplied to the patient mask, said supply conduit including a first end being received by the oxygen supply, said supply conduit including a second end positioned opposite said first end, said second end receiving an inlet port of the patient mask to allow oxygen supplied to said supply conduit to be supplied to a patient wearing the patient mask;

a side conduit being coupled to and being in fluid communication with said supply conduit, said side conduit extending substantially orthogonal to said supply conduit, said side conduit being positioned between said first end and said second end of said supply conduit, said side conduit including a flange being coextensive and extending outwardly from a free end of said side conduit;

an elbow conduit being rotatably coupled to said side conduit opposite said supply conduit, said elbow conduit being couplable to the nebulizer to permit treatments from the nebulizer to flow through said elbow conduit and said side conduit into the oxygen being supplied to the patient mask, said elbow conduit comprising;

a first portion being rotatably coupled to said free end of said side conduit to permit rotational adjustment of said elbow conduit with respect to said side conduit, said first portion being axially aligned with said side conduit, said first portion including a flange collar for receiving and extending around said flange of said side conduit to rotatably couple said elbow conduit to said side conduit;

a seal being positioned between said flange of said side conduit and said flange collar of said elbow conduit, said seal inhibiting fluid communication between an environment and the treatments passing through said elbow conduit and said side conduit;

a second portion being coupled to said first portion opposite said side conduit, said second portion extending substantially orthogonal to said first portion;

a receiving collar being coupled to said second portion opposite said first portion, said receiving collar receiving the nebulizer to selectively mount the nebulizer to said elbow conduit and permit treatments to be supplied to said elbow conduit;

a cap being couplable to said receiving collar to selectively close said receiving collar when the nebulizer is removed from said receiving collar;

a tether being coupled to said cap and extending around said second portion, said tether inhibiting loss of said cap when said cap is removed from said receiving collar; and a valve assembly being positioned in said elbow conduit between said side conduit and the nebulizer, said valve assembly opening to permit the treatments from the nebulizer to flow into said elbow conduit when air pressure from the nebulizer is greater than an air pressure in said supply conduit, said valve assembly closing to inhibit the treatments from entering said elbow conduit when the air pressure in said supply conduit is greater than the air pressure from the nebulizer.

* * * * *